United States Patent
Ellis et al.

(10) Patent No.: US 9,151,734 B2
(45) Date of Patent: Oct. 6, 2015

(54) CONNECTION ASSEMBLY FOR ULTRA HIGH PRESSURE LIQUID CHROMATOGRAPHY

(75) Inventors: Scott J. Ellis, Anacortes, WA (US); Troy N. Sanders, Oak Harbor, WA (US); Craig W. Graham, Anacortes, WA (US)

(73) Assignee: IDEX Health & Science LLC, Oak Harbor, WA (US)

(*) Notice: Subject to any disclaimer, the term of this patent is extended or adjusted under 35 U.S.C. 154(b) by 284 days.

(21) Appl. No.: 12/718,690

(22) Filed: Mar. 5, 2010

(65) Prior Publication Data

US 2010/0224546 A1     Sep. 9, 2010

Related U.S. Application Data

(63) Continuation-in-part of application No. 12/380,916, filed on Mar. 5, 2009, now abandoned.

(51) Int. Cl.
*B01D 35/00* (2006.01)
*G01N 30/60* (2006.01)

(52) U.S. Cl.
CPC ................................ *G01N 30/6039* (2013.01)

(58) Field of Classification Search
CPC .............................. G01N 30/6039; B01D 35/30
USPC ............. 210/635, 656, 659, 198.2, 232, 446, 210/450; 96/101; 277/608; 285/325, 327, 285/361, 376, 402
See application file for complete search history.

(56) References Cited

U.S. PATENT DOCUMENTS

| | | | | | |
|---|---|---|---|---|---|
| 3,298,396 | A | * | 1/1967 | Gressman et al. | 137/637.4 |
| 4,175,037 | A | * | 11/1979 | Benney et al. | 141/12 |
| 4,399,032 | A | * | 8/1983 | Mott | 210/198.2 |
| 4,469,597 | A | * | 9/1984 | Mott | 210/198.2 |
| 4,636,316 | A | * | 1/1987 | Harris et al. | 210/656 |
| 4,792,396 | A | * | 12/1988 | Gundelfinger | 210/198.2 |
| 5,377,939 | A | * | 1/1995 | Kirma | 248/68.1 |
| 5,395,196 | A | * | 3/1995 | Notaro | 411/396 |
| 5,472,598 | A | * | 12/1995 | Schick | 210/198.2 |

(Continued)

FOREIGN PATENT DOCUMENTS

| | | |
|---|---|---|
| EP | 1858611 B1 | 9/2011 |
| JP | S50-21320 A | 3/1975 |

(Continued)

OTHER PUBLICATIONS

PTO Translation No. 15-0084 of Sanuki (Japan Patent No. 03057588) Oct. 2014.*

(Continued)

*Primary Examiner* — Ernest G Therkorn
(74) *Attorney, Agent, or Firm* — Vinson & Elkins LLP

(57) ABSTRACT

A fitting assembly having a single- or double-headed ferrule, a nut, and a fitting that may be assembled or dissembled by an operator. The fitting assembly includes a nut with first and second ends, with the second end adapted to receive or abut the first end of a ferrule, and further includes a fitting with a first end having an internally tapered portion adapted to receive the second end of the ferrule and a second end adapted to be removably connected to a component or fitting of a liquid chromatography system. The nut, ferrule and fitting of the fitting assembly have passageways therethrough for receiving and removably holding tubing.

20 Claims, 9 Drawing Sheets

(56) References Cited

U.S. PATENT DOCUMENTS

| | | | |
|---|---|---|---|
| 5,525,303 A * | 6/1996 | Ford et al. | 422/535 |
| 5,582,723 A * | 12/1996 | Boone et al. | 210/198.2 |
| 5,601,785 A * | 2/1997 | Higdon | 422/546 |
| 5,730,943 A * | 3/1998 | Ford et al. | 422/535 |
| 5,938,919 A * | 8/1999 | Najafabadi | 210/198.2 |
| 6,095,572 A * | 8/2000 | Ford et al. | 285/361 |
| 6,361,687 B1 * | 3/2002 | Ford et al. | 210/198.2 |
| 6,772,656 B2 * | 8/2004 | Godoy et al. | 81/9.22 |
| 7,311,502 B2 * | 12/2007 | Gerhardt et al. | 417/390 |
| 7,314,505 B1 * | 1/2008 | Wheeler et al. | 95/83 |
| 7,316,777 B2 * | 1/2008 | Loy, Jr. | 210/198.2 |
| 8,011,867 B2 * | 9/2011 | Shepherd | 411/396 |
| 8,569,070 B2 * | 10/2013 | Ellis et al. | 436/161 |
| 2005/0077222 A1 * | 4/2005 | Dawes et al. | 210/198.2 |
| 2005/0269264 A1 * | 12/2005 | Fermier et al. | 210/635 |
| 2006/0113794 A1 * | 6/2006 | Plant et al. | 285/339 |
| 2006/0169628 A1 * | 8/2006 | Loy | 210/198.2 |
| 2006/0237353 A1 * | 10/2006 | Quimby et al. | 210/198.2 |
| 2007/0175809 A1 * | 8/2007 | Cao et al. | 210/198.2 |
| 2007/0283746 A1 * | 12/2007 | Gerhardt et al. | 73/61.56 |
| 2008/0001404 A1 * | 1/2008 | Nicholson | 285/339 |
| 2010/0224543 A1 * | 9/2010 | Ellis et al. | 210/198.2 |
| 2010/0224546 A1 * | 9/2010 | Ellis et al. | 210/232 |

FOREIGN PATENT DOCUMENTS

| | | |
|---|---|---|
| JP | S54-121418 A | 9/1979 |
| JP | S59-107391 U | 7/1984 |
| JP | H03-57588 U | 6/1991 |
| JP | 2004-036740 A | 2/2004 |

OTHER PUBLICATIONS

Upchurch Scientific Product Catalog, 2003, p. 10.
International Search Report, International Patent Application No. PCT/US2010/026387, Apr. 29, 2010.

* cited by examiner

CONNECTION ASSEMBLY FOR ULTRA HIGH PRESSURE LIQUID CHROMATOGRAPHY

CROSS-REFERENCE TO RELATED APPLICATION

This application is a continuation-in-part of U.S. patent application Ser. No. 12/380,916, filed Mar. 5, 2009, now abandoned, which is incorporated herein by reference in its entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention relates generally to an assembly for use in connecting components of liquid chromatography systems, and relates more particularly to an assembly well-suited for allowing quick connections and disconnections of components in liquid chromatography systems used in ultra-high pressure liquid chromatography.

2. Description of the Related Art

Liquid chromatography (LC) is a well-known technique for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase.

In a conventional LC system, the sample and mobile phase pass through one or more filters and often a guard column before coming to the column. A typical column usually consists of a piece of steel tubing which has been packed with a "packing" material. The "packing" consists of the particulate material "packed" inside the column. It usually consists of silica- or polymer-based particles, which are often chemically bonded with a chemical functionality. When the sample is carried through the column (along with the mobile phase), the various components (solutes) in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components.

Once the sample (with its components now separated) leaves the column, it flows with the mobile phase past a detector. The detector detects the presence of specific molecules or compounds. Two general types of detectors are used in LC applications. One type measures a change in some overall physical property of the mobile phase and the sample (such as their refractive index). The other type measures only some property of the sample (such as the absorption of ultraviolet radiation). In essence, a typical detector in a LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample.

In addition to the above components, a LC system will often include filters, check valves, a guard column, or the like in order to prevent contamination of the sample or damage to the LC system. For example, an inlet solvent filter may be used to filter out particles from the solvent (or mobile phase) before it reaches the pump. A guard column is often placed before the analytical or preparative column; i.e., the primary column. The purpose of such a guard column is to "guard" the primary column by absorbing unwanted sample components that might otherwise bind irreversibly to the analytical or preparative column.

In practice, various components in an LC system may be connected by an operator to perform a given task. For example, an operator will select an appropriate mobile phase and column, then connect a supply of the selected mobile phase and a selected column to the LC system before operation. In order to be suitable for high pressure liquid chromatography (HPLC) applications, each connection must be able to withstand the typical operating pressures of the HPLC system. If the connection is too weak, it may leak. Because the types of solvents that are sometimes used as the mobile phase are often toxic and because it is often expensive to obtain and/or prepare many samples for use, any such connection failure is a serious concern.

It is fairly common for an operator to disconnect a column (or other component) from a LC system and then connect a different column (or other component) in its place after one test has finished and before the next begins. Given the importance of leak-proof connections, especially in HPLC applications, the operator must take time to be sure the connection is sufficient. Replacing a column (or other component) may occur several times in a day. Moreover, the time involved in disconnecting and then connecting a column (or other component) is unproductive because the LC system is not in use and the operator is engaged in plumbing the system instead of preparing samples or other more productive activities. Hence, the replacement of a column in a conventional LC system involves a great deal of wasted time and inefficiencies.

Given concerns about the need for leak-free connections, conventional connections have been made with stainless steel tubing and stainless steel end fittings. More recently, however, it has been realized that the use of stainless steel components in a LC system have potential drawbacks in situations involving biological samples. For example, the components in a sample may attach themselves to the wall of stainless steel tubing. This presents problems because the detector's measurements (and thus the chromatogram) of a given sample may not accurately reflect the sample if some of the sample's components or ions remain in the tubing and do not pass the detector. Perhaps of even greater concern, however, is the fact that ions from the stainless steel tubing may detach from the tubing and flow past the detector, thus leading to potentially erroneous results. Hence, there is a need for "biocompatible" connections through the use of a material which is chemically inert with respect to such "biological" samples and the mobile phase used with such samples so that ions will not be released by the tubing and thus contaminate the sample.

In many applications using selector/injector valves to direct fluid flows, and in particular in liquid and gas chromatography, the volume of fluids is small. This is particularly true when liquid or gas chromatography is being used as an analytical method as opposed to a preparative method. Such methods often use capillary columns and are generally referred to as capillary chromatography. In capillary chromatography, both gas phase and liquid phase, it is often desired to minimize the internal volume of the selector or injector valve. One reason for this is that a valve having a large volume will contain a relatively large volume of liquid, and when a sample is injected into the valve the sample will be diluted, decreasing the resolution and sensitivity of the analytical method.

Micro-fluidic analytical processes also involve small sample sizes. As used herein, sample volumes considered to involve micro-fluidic techniques can range from as low as volumes of only several picoliters or so, up to volumes of several milliliters or so, whereas more traditional LC techniques, for example, historically often involved samples of about one microliter to about 100 milliliters in volume. Thus, the micro-fluidic techniques described herein involve volumes one or more orders of magnitude smaller in size than traditional LC techniques. Micro-fluidic techniques can also be expressed as those involving fluid flow rates of about 0.5 ml/minute or less.

Most conventional HPLC systems include pumps which can generate relatively high pressures of up to around 5,000 psi to 6,000 psi or so. In many situations, an operator can obtain successful results by operating a LC system at "low" pressures of anywhere from just a few psi or so up to 1,000 psi or so. More often than not, however, an operator will find it desirable to operate a LC system at relatively "higher" pressures of over 1,000 psi.

Another, relatively newer liquid chromatography form is Ultrahigh Pressure Liquid Chromatography (UHPLC) in which system pressure extends upward to 1400 bar or 20,000 psi. Both HPLC and UHPLC are examples of analytical instrumentation that utilize fluid transfer at elevated pressures. For example, in U.S. Patent Publication No. US 2007/0283746 A1, published on Dec. 13, 2007 and titled "Sample Injector System for Liquid Chromatography," an injection system is described for use with UHPLC applications, which are said to involve pressures in the range from 20,000 psi to 120,000 psi. In U.S. Pat. No. 7,311,502, issued on Dec. 25, 2007 to Gerhardt, et al., and titled "Method for Using a Hydraulic Amplifier Pump in Ultrahigh Pressure Liquid Chromatography," the use of a hydraulic amplifier is described for use in UHPLC systems involving pressures in excess of 25,000 psi. In U.S. Patent Publication No. US 2005/0269264 A1, published on Dec. 8, 2005 and titled "Chromatography System with Gradient Storage and Method for Operating the Same," a system for performing UHPLC is disclosed, with UHPLC described as involving pressures above 5,000 psi (and up to 60,000 psi). Applicants hereby incorporate by reference as if fully set forth herein U.S. Pat. No. 7,311,502 and US Patent Publications Nos. US 2007/0283746 A1 and US 2005/0269264 A1.

As noted, liquid chromatography systems, including HPLC or UHPLC systems, typically include several components. For example, such a system may include a pump; an injection valve or autosampler for injecting the analyte; a precolumn filter to remove particulate matter in the analyte solution that might clog the column; a packed bed to retain irreversibly adsorbed chemical material; the HPLC column itself; and a detector that analyzes the carrier fluid as it leaves the column. These various components may typically be connected by a miniature fluid conduit, or tubing, such as metallic or polymeric tubing, usually having an internal diameter of 0.003 to 0.040 inch.

All of these various components and lengths of tubing are typically interconnected by threaded fittings. Fittings for connecting various LC system components and lengths of tubing are disclosed in prior patents, for example, U.S. Pat. Nos. 5,525,303; 5,730,943; and 6,095,572, the disclosures of which are herein all incorporated by reference as if fully set forth herein. Often, a first internally threaded fitting seals to a first component with a ferrule or similar sealing device. The first fitting is threadedly connected through multiple turns by hand or by use of a wrench or wrenches to a second fitting having a corresponding external fitting, which is in turn sealed to a second component by a ferrule or other seal. Disconnecting these fittings for component replacement, maintenance, or reconfiguration often requires the use of a wrench or wrenches to unthread the fittings. Although a wrench or wrenches may be used, other tools such as pliers or other gripping and holding tools are sometimes used. In addition, the use of such approaches to connect components of an UHPLC system often results in deformation or swaging of a ferrule used to provide a leak proof seal of tubing to a fitting or component. This often means that the ferrule and tubing connection, once made, cannot be reused without a risk of introducing dead volumes into the system. In addition, such approaches may involve crushing or deformation of the inner diameter of the tubing, which may adversely affect the flow characteristics and the pressures of the fluid within the tubing. While hand-tightened threaded fittings eliminate the need for wrenches or other tools, these fittings typically can not stand up to the extreme pressures of HPLC or UHPLC.

Another approach to provide a connection in an UHPLC system involves providing a fitting assembly that uses a combination of components, including two separate ferrules. Such an approach is considered undesirable because by requiring two places for the ferrules to provide leak proof seals, it provides two places where the fluid to be analyzed may leak, as well as where dead volumes may be provided. In addition, this approach involves the use of additional components, which can cost more and also increase the time and effect to assemble them to make a connection or disassemble them when disconnecting tubing from a component or other fitting assembly.

It will be understood by those skilled in the art that, as used herein, the term "LC system" is intended in its broad sense to include all apparatus and components in a system used in connection with liquid chromatography, whether made of only a few simple components or made of numerous, sophisticated components which are computer controlled or the like. Those skilled in the art will also appreciate that an LC system is one type of an analytical instrument (AI) system. For example, gas chromatography is similar in many respects to liquid chromatography, but obviously involves a gas sample to be analyzed. Although the following discussion focuses on liquid chromatography, those skilled in the art will appreciate that much of what is said also has application to other types of AI systems and methods.

Therefore, it is an object of the present invention to provide a mechanism allowing an operator to quickly disconnect or connect a component of an UHPLC system.

It is another object of the present invention to provide a mechanism to reduce inefficiency and wasted time in connecting or disconnecting a component of an UHPLC system.

It is yet another object of the present invention to provide a mechanism to allow an operator to quickly replace a component of an UHPLC system.

It is yet another object of the present invention to provide a mechanism to allow an operator to quickly and easily achieve a leak-free connection of a component of an UHPLC system.

It is still another object of the present invention to provide a mechanism to minimize the risk of leakage or damage to the tubing of an UHPLC system.

It is still another object of the present invention to provide a biocompatible assembly to allow an operator to quickly and easily achieve a biocompatible connection of a component of an UHPLC system.

The above and other advantages of the present invention will become readily apparent to those skilled in the art from the following detailed description of the present invention, and from the attached drawings, which are briefly described below.

SUMMARY OF THE INVENTION

In a first embodiment of the invention, a fitting assembly is provided that is well-suited for use in liquid chromatography systems, and is particularly well-suited for use in high pressure liquid chromatography and ultra high pressure liquid chromatography. In this embodiment, the fitting assembly includes a nut with two ends and a passageway therethrough, a double-headed ferrule having a passageway therethrough, and a fitting having first and second ends and having a passageway therethrough. The passageways through the nut, ferrule, and fitting are adapted to receive and removably hold tubing in this embodiment. In addition, the second end of the nut has an interior portion which is tapered and adapted to receive the first end of the ferrule. In addition, the first end of the fitting has an interior portion which is tapered and adapted to receive the second end of the ferrule. The interior portion of the nut also has internal threads adapted to mate and engage with an externally threaded portion near the first end of the fitting. When the internal threaded portions of the nut and the external threads of the fitting are engaged, the nut, ferrule and fitting provide a leak proof fitting assembly holding tubing therein and removably securing the tubing to a port of an LC or AI system or other fitting or component of an LC or AI system. In another embodiment of the fitting assembly, the nut, ferrule and fitting, as well as the tubing, may be made of a polymeric material, such as polyetheretherketone (PEEK), or other biocompatible materials. In another embodiment, the nut and fitting may be made of PEEK or another biocompatible polymer, while the ferrule is made of a metal, such as stainless steel. In another embodiment, a UHPLC system is provided which includes at least one fitting assembly comprising a nut, ferrule, and fitting as described to provide a connection for fluid flow between at least two components or fittings of the UHPLC system. In yet another alternative embodiment, the assembly may comprise a ferrule having externally tapered first and second ends in which at least one of said tapered ends is defined by a plurality of tapered members with gaps between at least a portion of the tapered members.

In still another embodiment, a method of assembling a fitting assembly is provided, by which an operator can easily connect tubing to a component or fitting of an LC or other AI system. In one embodiment, an operator can insert tubing through the passageways of a nut, a double-headed ferrule, and a fitting, such as those described above and in more detail below. The operator can then rotate the nut and the fitting relative to one another, such as by rotating the fitting in a clockwise motion when viewed from the second end of the fitting. Alternatively, the operator can turn the nut relative to the fitting. By turning the nut and fitting relative to one another, the threaded external portions of the fitting engage with the internal threaded portions of the nut, pushing the first end of the ferrule towards and against the tapered portion of the nut, and pushing the internal tapered portion of the fitting towards and against the second end of the ferrule, thereby providing a fitting assembly providing a leak proof seal between the tubing and the component or fitting of the LC or other AI system.

The present disclosure also provides a fitting assembly for use in a liquid chromatography system, comprising a nut having a first end and a second end, and having a passageway therethrough, wherein the passageway has a tapered portion, and wherein the second end of the nut has an externally threaded portion, a ferrule having a first externally tapered end and a second externally tapered end and having a passageway therethrough, and a fitting having a first end and a second end and having a passageway therethrough, wherein the first end of the fitting has an internally threaded portion and an internally tapered portion, and wherein the internally threaded portion of the fitting is adapted to securely engage with the externally threaded portion of the nut, and wherein the internally tapered portion of the fitting is adapted to receive and hold the second tapered end of the ferrule. In certain embodiments of the assembly, the fitting further comprises an external tapered portion located at or near the second end of the fitting, while in other embodiments the fitting further comprises an externally threaded portion which is located between the first end of the fitting and the second end of the fitting. In particular embodiments the nut, the fitting, and/or the ferrule comprises a polymer. In further embodiments the fitting assembly consists essentially of biocompatible materials. In additional embodiments at least one of the first end and the second end of the ferrule comprises a plurality of members. In yet other embodiments at least one tube extends through the passageways of the nut, the ferrule, and the fitting. In alternative embodiments the passageway through the nut, the ferrule, and/or the fitting is coated. In such embodiments the passageway through the nut, the ferrule, or the fitting can be coated with a nickel, silica carbide, copper or diamond coating, or a combination thereof.

The disclosure additionally provides a fitting assembly for use in a liquid chromatography system, comprising, a nut having a first end and a second end, and having a passageway therethrough, wherein the second end of the nut has an externally threaded portion, a ferrule having a first end and a second externally tapered end and having a passageway therethrough, a fitting having a first end and a second end and having a passageway therethrough, wherein the first end of the fitting has an internally threaded portion and an internally tapered portion, and wherein the internally threaded portion of the fitting is adapted to securely engage with the externally threaded portion of the nut, and wherein the internally tapered portion of the fitting is adapted to receive and hold the second externally tapered end of the ferrule, and wherein the second end of the fitting defines an opening, and a ferrule tip having a first end and an externally tapered second end, wherein the first end of the ferrule tip is adapted to securely engage with the opening in the second end of the fitting. In certain embodiments the passageway through the nut, the ferrule, the fitting, and or the ferrule tip is coated, for example with a nickel, silica carbide, copper or diamond coating, or a combination thereof. In additional embodiments the fitting assembly further comprises a knurl head having a first end and a second end and a passageway therethrough, wherein the second end of the knurl head defines an opening adapted to securely engage with the first end of the nut. In particular embodiments the passageway through the knurl head is coated.

The present disclosure further provides a fitting assembly for use in a liquid chromatography system, comprising a nut having a first end and a second end, and having a passageway therethrough, wherein the passageway has a tapered portion, and wherein the second end of the nut has an internally threaded portion, a ferrule having a first externally tapered end and a second externally tapered end and having a passageway therethrough, and a fitting having a first end and a second end and having a passageway therethrough, wherein the first end of the fitting has an externally threaded portion and an internally tapered portion, and wherein the externally threaded portion of the fitting is adapted to securely engage with the internally threaded portion of the nut, and wherein the internally tapered portion of the fitting is adapted to receive and hold the second tapered end of the ferrule, wherein the passageway through the nut, the ferrule, or the fitting is coated. In certain embodiments the passageway through the nut, the ferrule, or the fitting is coated with a nickel, silica carbide, copper or diamond coating, or a combination thereof.

In addition, the present disclosure provides an ultra high pressure liquid chromatography system comprising at least one fitting assembly having a nut having a first end and a second end, and having a passageway therethrough, wherein the passageway has a tapered portion, and wherein the second end of the nut has an externally threaded portion, a ferrule having a first externally tapered end and a second externally tapered end and having a passageway therethrough, and a fitting having a first end and a second end and having a passageway therethrough, wherein the first end of the fitting has an internally threaded portion and an internally tapered portion, and wherein the internally threaded portion of the fitting is adapted to securely engage with the externally threaded portion of the nut, and wherein the internally tapered portion of the fitting is adapted to receive and hold the second tapered end of the ferrule. In particular embodiments of the system the passageway through the nut, the ferrule, or the fitting is coated.

Furthermore, the present disclosure provides an ultra high pressure liquid chromatography system comprising at least one fitting assembly having a nut having a first end and a second end, and having a passageway therethrough, wherein the second end of the nut has an externally threaded portion, a ferrule having a first end and a second externally tapered end and having a passageway therethrough, a fitting having a first end and a second end and having a passageway therethrough, wherein the first end of the fitting has an internally threaded portion and an internally tapered portion, and wherein the internally threaded portion of the fitting is adapted to securely engage with the externally threaded portion of the nut, and wherein the internally tapered portion of the fitting is adapted to receive and hold the second externally tapered end of the ferrule, and wherein the second end of the fitting defines an opening, and a ferrule tip having a first end and an externally tapered second end, wherein the first end of the ferrule tip is adapted to securely engage with the opening in the second end of the fitting. In additional embodiments the system further comprises a knurl head having a first end and a second end and a passageway therethrough, wherein the second end of the knurl head defines an opening adapted to securely engage with the first end of the nut. In certain embodiments of the system the passageway through the nut, the ferrule, the fitting, the ferrule tip, and/or the knurl head is coated.

The present disclosure also provides an ultra high pressure liquid chromatography system comprising at least one fitting assembly having a nut having a first end and a second end, and having a passageway therethrough, wherein the passageway has an internal tapered portion, and wherein the second end of the nut has an internally threaded portion, a ferrule having a first tapered end and a second tapered end and having a passageway therethrough, and a fitting having a first end and a second end and having a passageway therethrough, wherein the first end of the fitting has an externally threaded portion and wherein the second end of the fitting has an external tapered portion, and wherein the externally threaded portion of the fitting is adapted to securely engage with the internally threaded portion of the nut, and wherein an internally tapered portion of the fitting is adapted to receive and hold the second tapered end of the ferrule when the externally threaded portion of the fitting is engaged with the internally threaded portion of the nut, wherein the passageway through the nut, the ferrule, or the fitting is coated. These and other embodiments and advantages are described below.

DETAILED DESCRIPTION

Figure 1:
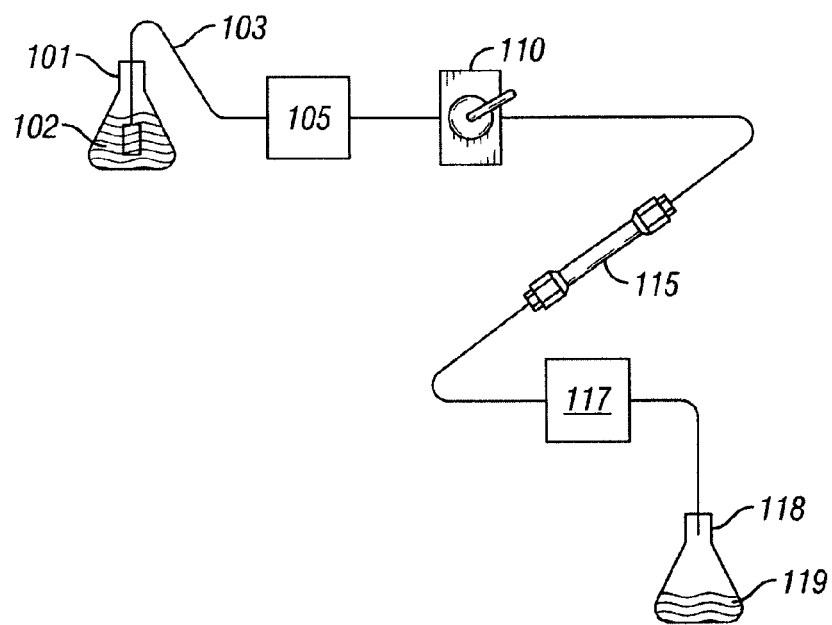
FIG. 1 is a block diagram of a conventional LC system.

In FIG. 1, a block diagram of the essential elements of a conventional LC system is provided. A reservoir 101 contains a solvent or mobile phase 102. Tubing 103 connects the mobile phase 102 in the reservoir 101 to a pump 105. The pump 105 is connected to a sample injection valve 110 which, in turn, is connected via tubing to a first end of a guard column (not shown). The second end of the guard column (not shown) is in turn connected to the first end of a primary column 115. The second end of the primary column 115 is then connected via tubing to a detector 117. After passing through the detector 117, the mobile phase 102 and the sample injected via injection valve 110 are expended into a second reservoir 118, which contains the chemical waste 119. As noted above, the sample injection valve 110 is used to inject a sample of a material to be studied into the LC system. The mobile phase 102 flows through the tubing 103 which is used to connect the various elements of the LC system together.

When the sample is injected via sample injection valve 110 in the LC system, the sample is carried by the mobile phase through the tubing into the column 115. As is well known in the art, the column 115 contains a packing material which acts to separate the constituent elements of the sample. After exiting the column 115, the sample (as separated via the column 115) then is carried to and enters a detector 117, which detects the presence or absence of various chemicals. The information obtained by the detector 117 can then be stored and used by an operator of the LC system to determine the constituent elements of the sample injected into the LC system. Those skilled in the art will appreciate that FIG. 1 and the foregoing discussion provide only a brief overview of a simplistic LC system that is conventional and well known in the art, as is shown and described in U.S. Pat. No. 5,472,598, issued Dec. 5, 1995 to Schick, which is hereby incorporated by reference as if fully set forth herein.

Preferably, for an LC system to be biocompatible, the various components (except where otherwise noted) that may come into contact with the effluent or sample to be analyzed are made of the synthetic polymer polyetheretherketone, which is commercially available under the trademark "PEEK" from ICI Americas. The polymer PEEK has the advantage of providing a high degree of chemical inertness and therefore biocompatibility; it is chemically inert to most of the common solvents used in LC applications, such as acetone, acetonitrile, and methanol (to name a few). PEEK also can be machined by standard machining techniques to provide smooth surfaces.

Figure 2:
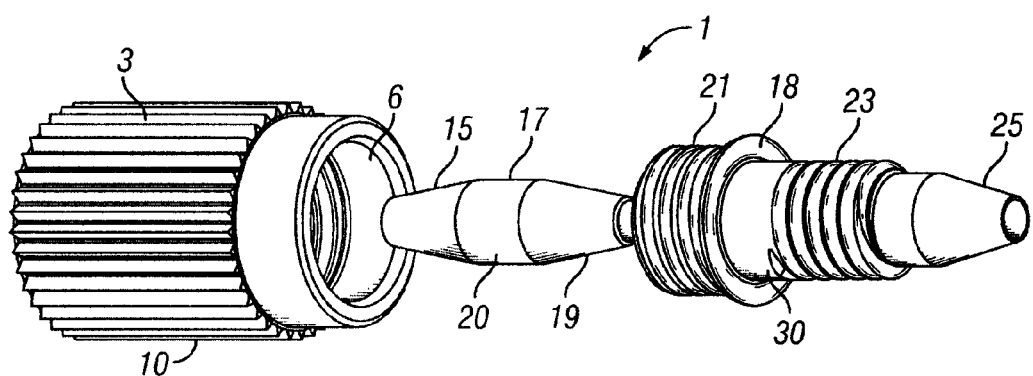
FIG. 2 is an exploded view of various components of an embodiment of an assembly in accordance with one aspect of the present invention.

Referring now to FIG. 2, a first embodiment of an assembly or fitting 1 is shown. As shown in FIG. 2, the assembly 1 includes a nut 10, a double-headed ferrule 20, and a fitting 30. As shown in FIG. 2, each of nut 10, ferrule 20, and fitting 30 are generally circular and symmetric about a center axis. The outer diameter of a first end of the nut 10 includes ridges 3 that form a knurled portion of the outer diameter of the nut 10 at one end. These are provided to allow an operator to more easily grip and turn the nut 10. The other or second end of the nut 10 includes an open interior portion 6. As detailed below, the open or interior portion 6 is adapted to receive and securely hold a combination of a first end of the ferrule 20 and a first end of the fitting 30. As shown in FIG. 2, each of nut 10, ferrule 20, and fitting 30 defines an essentially circular shape around an axis. Those skilled in the art will realize that a circular shape has advantages, but the outer diameters in particular of nut 10 may have a non-circular shape if desired, such as flat or concave portions to allow an operator to easily grip and rotate same.

Still referring to FIG. 2, it can be seen that the ferrule 20 as shown has three relatively distinct portions. These include a first end portion 15, a middle portion 17, and a second end portion 19. Each of end portions 15 and 19 has a tapered portion of the outer diameter so that each of the tapered portions forms a truncated conical shape. As shown in FIG. 2, the taper of the tapered portions 15 and 19 defines an angle from the axis of the ferrule 20. As shown in FIG. 2, the tapered portions 15 and 19 essentially have the same angle from the axis of ferrule 20. However, those skilled in the art will appreciate that the tapered portions 15 and 19 can define different angles if desired. As detailed below, each of tapered portions 15 and 19 are adapted to be removably received in interior portions of nut 10 and fitting 30, respectively.

The fitting 30 is also shown in FIG. 2. Fitting 30 includes two separate ends. A first end portion 21 includes external threads located on the outer diameter of the first end portion 21 of the fitting 30. A middle portion 23 of the fitting 30 includes a second set of external threads also located on the outer diameter of the fitting 30. A second end portion 25 of the fitting 30 includes a tapered portion on the outer diameter of the fitting 30 that is shaped as a truncated cone. As detailed below, the threaded portion 23 of the fitting 30 is adapted to be removably secured to corresponding threaded portion 6 of a port or a fitting of an LC or other analytical instrument (AI) system (not shown) or to another fitting or component of an LC or other AI system. Those skilled in the art will appreciate that the tapered portion 25 and the threaded portion 23 of the fitting 30 may be adapted so that they removably engage with a standard port of an LC or other AI system (not shown). The fitting 30 also includes a shoulder portion 18. As shown in FIG. 2, the shoulder 18 has a greater outer diameter than the threaded portion 21 of the fitting 30. The shoulder 18 is discussed in more detail below.

Figure 3:
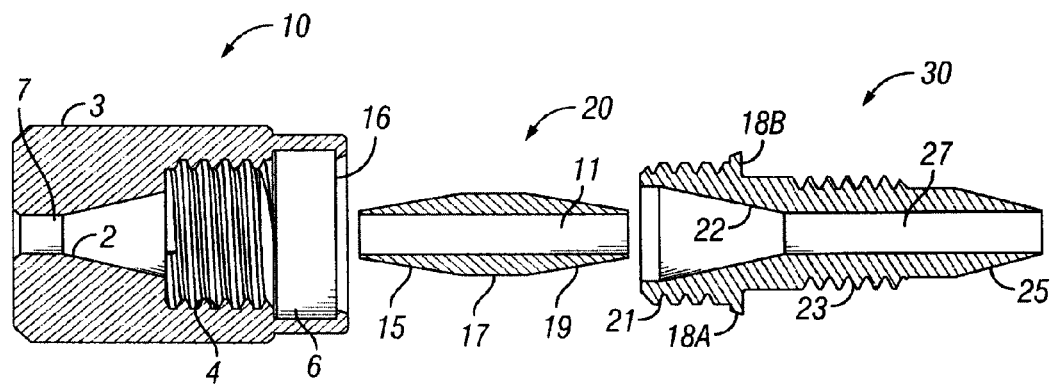
FIG. 3 is an exploded cross-sectional view of the assembly of FIG. 1

Now referring to FIG. 3, additional details regarding the nut 10, ferrule 20, and fitting 30 are provided. Like features and elements in the drawings have the same numerals in the various figures. FIG. 3 provides an exploded cross-sectional view of nut 10, ferrule 20 and fitting 30. Each of nut 10, ferrule 20, and fitting 30 have internal passageways 7, 11, and 27 extending therethrough, respectively. The passageways 7, 11, and 27 are adapted to allow tubing (not shown) to extend through each of nut 10, ferrule 20, and fitting 30, and thus through the assembly 1.

As shown in FIG. 3, nut 10 has a first end and a second end, and includes an interior portion 6 at its second end. A portion of the interior portion 6 includes a threaded portion 4, in which the internal wall of the nut 10 in the threaded portion 4 provides threads. In addition, the nut 10 includes an internal tapered portion 2. The tapered portion 2 of the nut 10 is adapted to receive and securely hold the first end portion 15 of the ferrule 20 when the assembly 1 is made. The threads of the threaded portion 4 of the nut 10 are adapted to removably receive and securely hold the threaded portion 21 of the fitting 30 when the assembly 1 is connected. The nut 10 includes an opening 16 at the second end of nut 10 (shown on the right hand side of FIG. 3). As shown in FIG. 3, the opening 16 has an angular cross-section, such that the outer diameter of the opening 16 is greater at the second end of the nut 10 than it is at the opening to the interior portion 6 of the nut 10.

In FIG. 3, it can be seen that the fitting 30 has a first end and a second end, and further has an internal tapered portion 22 at the first end, opposite the end portion 25 of the second end of the fitting 30. The end portion 25 of fitting 30 is tapered externally. The internally tapered portion 22 of the fitting 30 is adapted to receive and removably hold the end portion 19 of the ferrule 20 when the assembly 1 is made. The fitting 30 further includes a shoulder 18, which includes both an angularly shaped portion 18a and a substantially flat retaining portion 18b. As shown in FIG. 3, the angular portion 18a of the shoulder 18 defines an angle such that the outer diameter of the shoulder 18 is greater at the end of the shoulder 18 that is furthest from the first end of the fitting 30 (shown on the left hand side of the fitting 30 in FIG. 3).

With respect to the ferrule 20 shown in FIG. 3, the ferrule 20 has a first end with an externally tapered portion 15, a middle portion 17 which, as shown in FIG. 3, is not tapered, and a second end with an external taper portion 19. As noted above, each of nut 10, ferrule 20, and fitting 30 have internal passageways 7, 11, and 27, respectively, which are adapted to removable receive and hold tubing (not shown in FIG. 3). Although not shown, it will be appreciated that the angles of tapered portions 15 and 19 of the ferrule 20 from the axis of ferrule 20 may differ from the angles defined by the tapered portions 2 and 22 of the nut 10 and the fitting 30, respectively. For example, the angles defined by the tapered portions 15 and 19 may be greater than the angles defined by tapered portions 2 and 22, respectively, to make it easier to obtain sufficient tubing retention with assembly 1 when nut 10, ferrule 20, and fitting 30 are engaged and assembled.

Figure 4:
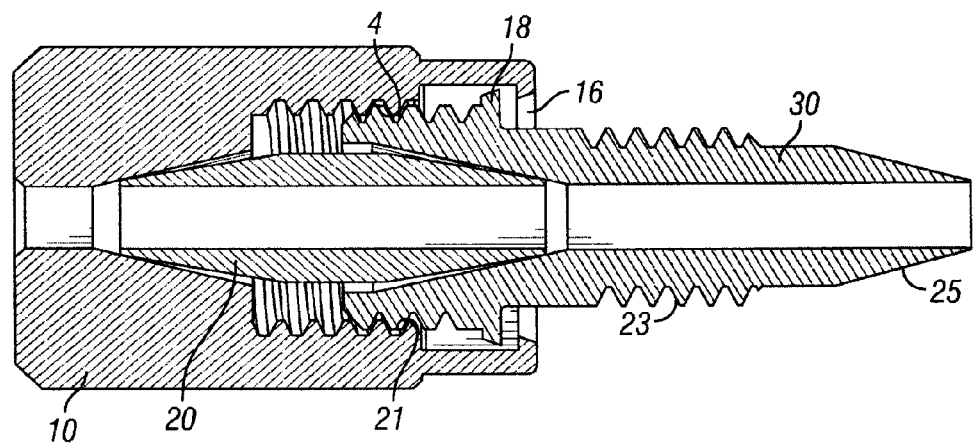
FIG. 4 is a cross-sectional view of the assembly of FIG. 1 when connected.

Referring now to FIG. 4, a cross-sectional view of the assembly 1 as connected by an operator is shown. As shown in FIG. 4, the nut 10, ferrule 20, and fitting 30 are removably secured to one another. At least a portion of the internal threaded portion 4 of the nut 10 receives and holds at least a portion of the external threaded portion 21 of the fitting 30. As noted above, the threaded portions 4 and 21 are each adapted to mate with each other, such that a connection can easily be made as shown in FIG. 4. As also shown in FIG. 4, at least a portion of the fitting 30 extends from the interior portion 6 of the nut 10. As shown in FIG. 4, the fitting 30 includes a threaded portion 23 of the portion of the fitting 30 that extends outward from the nut 10, as well as a tapered portion 25. The tapered portion 25 of the fitting 30 is adapted to fit within a port (not shown) of an LC or other AI component or fitting, and the threaded portion 23 is adapted to mate with an internally threaded portion (not shown) of the port of an LC system component or a fitting or other component of an LC or other AI system.

Still referring to FIG. 4, it will be seen that the shoulder 18 of the fitting 30 is located within the interior portion 6 of the nut 10. As shown in FIG. 4, it will be appreciated that the smallest outer diameter of the shoulder 18a is about the same or slightly less than the largest outer diameter of the opening 16 of the nut 10. In addition, the largest outer diameter of the shoulder portion 18 of the fitting 30 is greater than the smallest outer diameter of the opening 16 of the nut 10. Thus, once the shoulder 18 of the fitting 30 has passed entirely through opening 16 of the nut 10, the shoulder 18 and opening 16 are of such shapes and sizes that the first end of the fitting 30 will be retained within the interior portion 6 of the nut 10 unless an operator exerts some additionally significant effort to separate the nut 10 and fitting 30 from one another. Thus, the shoulder 18 and opening 16 are adapted so that, once the assembly 1 is connected, the components of the assembly 1 are retained together for easier use by an operator.

Figure 5:
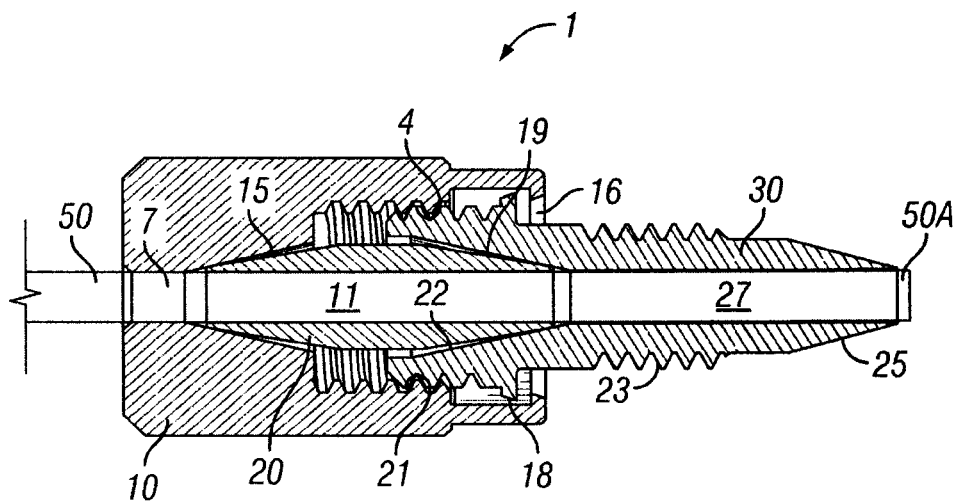
FIG. 5 is a cross-sectional view of the assembly of FIG. 4 that includes tubing.

Referring now to FIG. 5, a cross-sectional view of an assembly 1 is provided. The view of assembly 1 shown in FIG. 5 differs from that shown in FIG. 4 in that the assembly 1 in FIG. 5 includes tubing 50 extending through the passageways 7, 11, and 27 of the nut 10, ferrule 20 and fitting 30, respectively. In FIG. 5, the tubing 50 is shown as a single piece which is of a size having an appropriate outer diameter that fits easily within the passageways 7, 11, and 27. As shown in FIG. 5 a portion 50a of the tubing 50 extends a slight distance from the second end of the fitting 30 (shown on the right side of FIG. 5). Those skilled in the art will appreciate that, depending on the size and shape of the port of a LC system component or fitting to which assembly 1 is to be connected (such as via engaging threads 23 of the fitting 30 with threads of a port (not shown), more of tubing 50 may extend than is shown as portion 50a or, in some cases, it may be desirable to have no portion 50a of the tubing 50 extend outwardly past the second end of the fitting 30. In general, we believe that the threads 23 and shape and size of the tapered portion 25 of the fitting 30 should be of a shape and size so that fitting 30 may be easily secured to a port of a LC system component or fitting and may also be easily removed therefrom, in either case by rotating the fitting 30 (and assembly 1) relative to the port.

Figure 8:
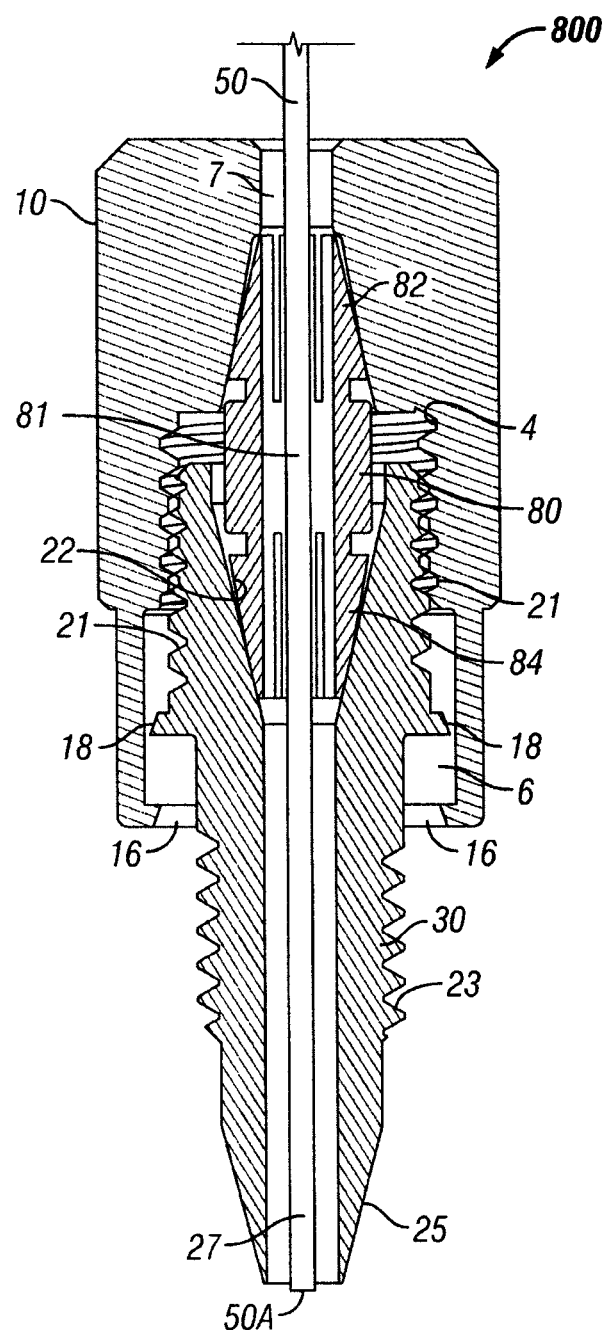
FIG. 8 is a cross-sectional view of an alternative embodiment of an assembly.

Generally, the rotational force or torque applied to connect to the nut 10, ferrule 20, fitting 30 and tubing 50 (such as shown in FIG. 5) to a port or other fitting of a component in an LC system accomplishes two major tasks. First, the force of the connection of the assembly 1 needs to be sufficient to provide a sealed and leakproof connection to the port or other fitting. In addition, the force of the connection of the assembly 1 needs to be sufficient so that the tubing 50 is securely held and is sufficient to prevent detachment due to the hydraulic force of the fluid moving through the tubing 50. We believe that the latter function typically involves greater forces than the former. We believe that the assembly 1 (such as shown in FIG. 5) and assembly 800 (such as shown in FIG. 8) provide an advantage in that they allow for better connections at higher pressures without requiring higher forces to connect assembly 1 or assembly 800.

It will be appreciated that the nut 10, ferrule 20, and fitting 30 can comprise a number of different materials. For example, each of nut 10, ferrule 20 and fitting 30 in an assembly 1 can comprise a metal, such as stainless steel, or each can comprise a different material, such as a polymer. For example, the assembly 1 can comprise a nut 10 comprising PEEK, a ferrule 20 comprising stainless steel, and a fitting 30 comprising PEEK. It will be appreciated that a variety of metals and polymers may be selected for any one or more of nut 10, ferrule 20, and fitting 30 depending on the particular application, as that may involve a particular type of sample, a particular type of solvent, and/or a particular pressure range. In addition, the selection of materials for the tubing may lead to a selection of a particular material for nut 10, ferrule 20, and/or fitting 30. In addition, PEEK (or other polymers) may be used that is reinforced with carbon fibers or steel fibers, or the like. Other polymer materials which may be used include TEFLON, TEFZEL, DELRIN, PPS, polypropylene, and others, depending on the foregoing factors and perhaps others, such as cost. Those skilled in the art will further appreciate that assembly 1 is shown as a fitting connection for connecting tubing to another component in an LC or other AI system, and that the other component may be any one of wide variety of components. Such components include pumps, columns, filters, guard columns, injection valves and other valves, detectors, pressure regulators, reservoirs, and other fittings, such as unions, tees, crosses, adapters, splitters, sample loops, connectors, and the like.

In order for a fitting to seal, it should generally remain in compression (relative to the conical surface of the port) throughout all environmental conditions. Therefore, in certain aspects a coating with a high coefficient of friction between the outer surface of the tube material is applied to the internal bore surface of the described fitting connection or assembly 1. The high coefficient of friction between the outer surface of the tube and the internal bore surface of the fitting connection or assembly 1 keeps the tube from extruding out of the port during pressurization, which results in dramatically increased burst pressure. In such embodiments the fitting connection or assembly is coated at the internal bore surface that contacts the tube starting at approximately 0.005 inches, about 0.0075 inches, about 0.01 inches, or about 0.02 inches from the tip. Coatings suitable for use with the presently described fitting connection or assembly include, but are not limited to, nickel, silica carbide, copper, and diamond coatings, and combinations thereof.

Methods of using the fitting connection or assembly 1 (such as shown in FIGS. 2-5) are now described in further detail. An operator can first provide a nut 10, ferrule 20 and fitting 30, as well as tubing (not shown). In one approach, the operator can insert a portion of the tubing through the passageways in nut 10, ferrule 20 and fitting 30 in that order without assembling or otherwise connecting any of nut 10, ferrule 20 and fitting 30. Next, the operator inserts a first end of the ferrule 20 into the second end of the nut 10 and pushes the first end of the ferrule 20 against the internal tapered portion of the nut 10. Next, the operator inserts the first end of the fitting 30 into the interior portion 6 of the nut 10. The operator then pushes the first end of the fitting 30 into the second end of the nut 10 (and/or against the second end of the ferrule 20) until the external threads 21 of the fitting 30 meet the internally threads 4 of the nut 10. Once the threads 21 and 4 of the fitting 30 and the nut 10 begin to mate or engage, the operator then rotates the fitting 30 relative to nut 10, rotates the nut 10 relative to fitting 30, or rotates both the nut 10 and fitting 30 relative to each other. By so rotating the nut 10 and fitting 30 relative to one another, the operator drives the fitting 30 further into the interior portion 6 of the nut 10. In doing so, the operator thus forces the first end 15 of the ferrule 20 against the internally tapered portion 2 of nut 10 and also forces the internally tapered portion 22 of the first end of fitting 30 against the second tapered end 19 of the ferrule 20. In doing so, the tapered first and second ends 15 and 19, respectively, of the ferrule are compressed and held firmly against portions 2 and 22 of the nut 10 and the fitting 30, respectively, thereby forming a leak proof connection. Because the first and second ends 15 and 19 of the ferrule 20 may be deformed or compressed as they are forced against the tapered portions 2 and 22 of the nut 10 and fitting 30, respectively, a leak proof connection may be obtained by the operator without the use of additional tools such as a wrench, pliers or the like.

To disconnect an assembly 1, such as shown in FIG. 4, an operator may either rotate the fitting 30 relative to nut 10, rotate nut 10 relative to fitting 30, or rotate both nut 10 and fitting 30 relative to each other. By rotating nut 10 and/or fitting 30 relative to one another, the operator thus rotates the threaded portions 21 and 4 of nut 10 and fitting 30, respectively, and thereby moves the first end of the fitting 30 away from the second end of the nut 10, and releases the connection between such threaded portions 21 and 4. By doing so, the operator thus relieves the forces that push the first end 15 of the ferrule against the internal tapered portion 2 of the nut 10, as well as the tapered portion 22 of the fitting 30 against the second end 19 of the ferrule 20. At this point, the operator can use the assembly 1 and the leak proof connection it provides, until the operator decides to remove the tubing (not shown) from the assembly 1. Alternatively, the operator can disconnect the entire assembly 1 from a port of an LC or other AI system (not shown) by rotating the nut 10. By selecting the direction of the threading of the threaded portions 4 and 21 of the nut 10 and fitting 30, respectively, the operator can turn the entire assembly 1 (when connected) by turning or rotating nut 10, such that the fitting 30 rotates relative to the port (not shown) and disengages therefrom. Thus, the entire assembly 1 is easily disconnected from the port (not shown).

Figure 6:
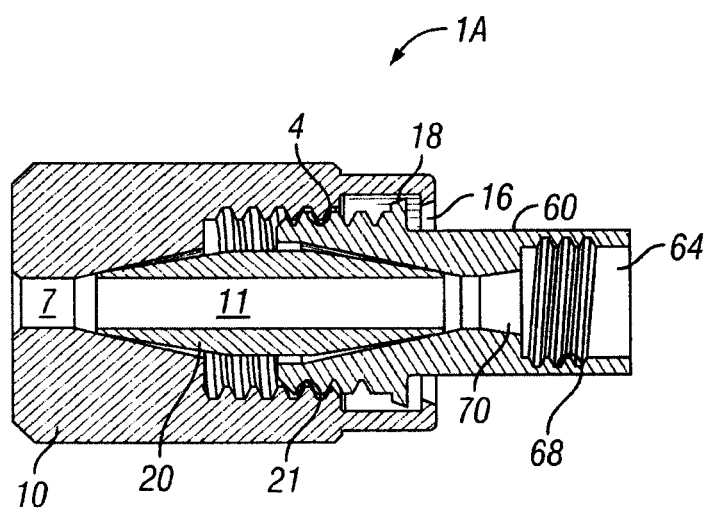
FIG. 6 is a cross-sectional view of an alternative embodiment of an assembly.

Referring now to FIG. 6, an alternative embodiment of an assembly 1a is illustrated. In FIG. 6, an assembly 1a is shown. Like the assembly 1 of FIG. 4, the assembly 1a of FIG. 6 includes a nut 10 and a double-headed ferrule 20, each of which has the same features as previously described. However, instead of fitting 30 (such as shown in FIG. 4), the assembly 1a includes fitting 60. As shown in FIG. 6, fitting 60 includes an interior portion 64 at its second end (shown on the right hand side of FIG. 6). Fitting 60 also has internal threads 68, as well as an internal tapered portion 70. Fitting 60 is adapted to threadably engage an external port (not shown) of a LC system component or fitting, which can fit within the interior portion 64 of the fitting 60. By rotating the fitting 60 (and the assembly 1a if assembled together), an operator can connect the fitting 60 to the port (not shown). When connected, it is expected that a portion of the port will be securely held in the tapered portion 70 by the engagement of the threads 68 with those of the external threads (not shown) of the external port (not shown). When the operator wishes to disconnect the fitting 60 (and the assembly 1a if assembled) from the port (not shown), the operator simply rotates the fitting 60 (and assembly 1a, as the case may be) relative to the port (not shown). As FIG. 6 shows, the use of external threads on one element, such as the fitting 60, versus internal threads, is a matter of selection. Those skilled in the art will therefore appreciate that the nut 10 in an alternative embodiment could have external threads (not shown) located near a second end which could be engaged with internal threads (not shown) located near the first end of an alternative embodiment of fitting 30.

Figure 7A:
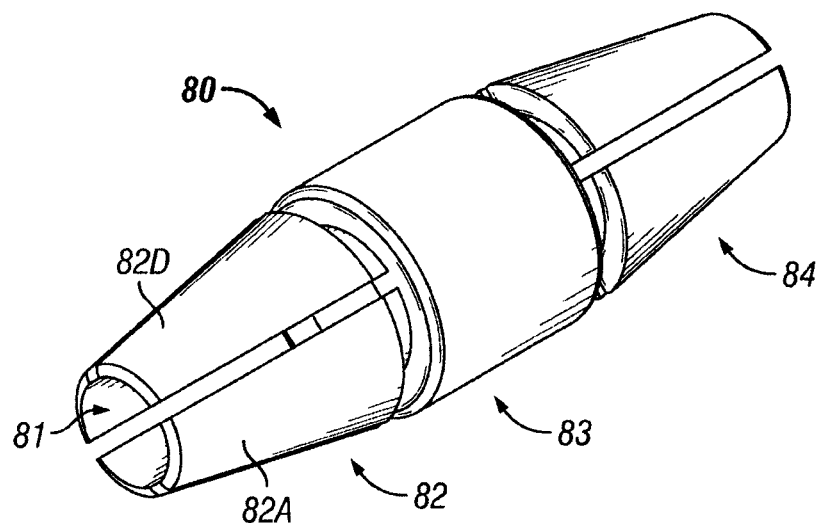
FIG. 7A, FIG. 7B, and FIG. 7C are, respectively, an isometric view, a frontal view, and a cross-sectional view of a ferrule in an alternative embodiment.
Figure 7B:
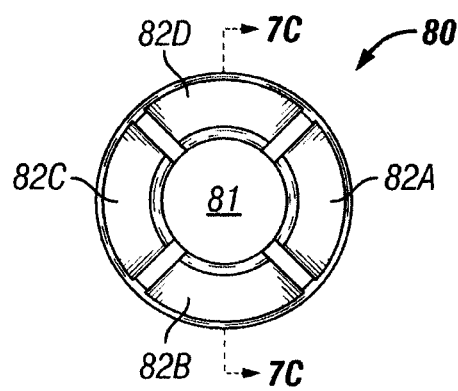
Figure 7C:
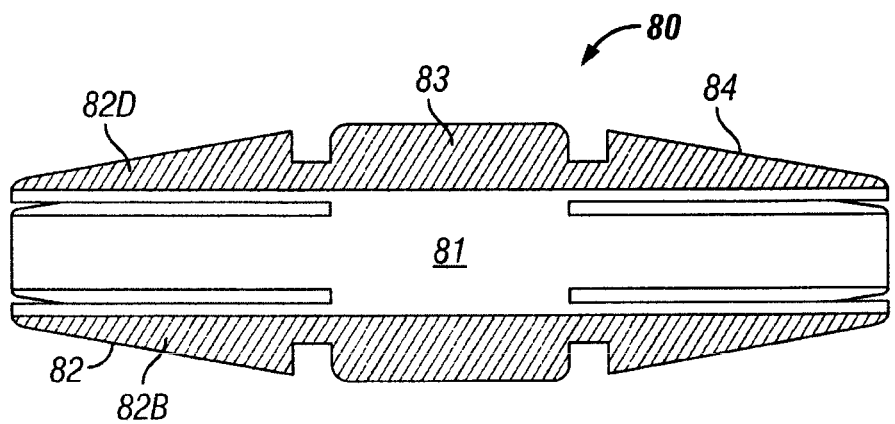

Referring now to FIG. 7A, FIG. 7B, and FIG. 7C, an alternative embodiment of a ferrule 80 is shown. It will be appreciated that ferrule 80 can be used in place of ferrule 20 as shown in FIGS. 2-6 and discussed above. As shown in FIG. 7A, the ferrule 80 has three relatively distinct portions: a first end portion 82, a middle portion 83, and a second end portion 84. As shown in FIG. 7A, the ferrule 80 also has a passageway 81 extending therethrough for receiving and releaseably holding tubing (not shown in FIG. 7A). The first end 82 of the ferrule 80 also has four distinct members, with members 82a and 82d shown most clearly in FIG. 7A.

Now referring to FIG. 7B, a frontal view of the first end 82 of the ferrule 80 is provided. As shown in FIG. 7B, the ferrule 80 is circular and has a passageway 81 extending therethrough. The first end 82 of the ferrule 80 is defined by members 82a, 82b, 82c, and 82d. It will be appreciated that the first end 82 of the ferrule could be defined, alternatively, by more or less than four members. As shown in FIG. 7A and FIG. 7B, the members 82a-82d define a truncated conical shape of the first end 82 of the ferrule 80. The angle defined by the taper of the members 82a-82b may be the same as described above with respect to ferrule 20. As also shown, there are gaps between each of the members 82a-82d. These gaps are considered advantageous in that they allow for easier movement of the members 82a-82d when the first end 82 of the ferrule 80 is compressed.

In FIG. 7C, a cross-sectional view of the ferrule 80 is provided along line G-G. In FIG. 8C, the first end portion 82, middle portion 83, and second end portion 84 of the ferrule are shown. The external tapers of the first end portion 82 and the second end portion 84 are also shown in FIG. 7C. Passageway 81 through ferrule 80 is also shown. In addition, members 82b and 82d are indicated in FIG. 7C. Although not numbered separately, it will be understood that the second end portion 84 of the ferrule 80 likewise has four separate members (like 82a-82d) which define a truncated conical shape, and define the external tapered portion of the second end portion 84 of the ferrule 80. Although not shown, it will be appreciated that the first end portion 82 and second end portion 84 may have more or less than four members and may have differing numbers of members than each other.

Referring now to FIG. 8, an alternative embodiment of an assembly 800 is shown. It will be appreciated that the assembly 800 is similar to the assembly 1 shown in FIG. 5 and described above, except that the assembly 800 includes ferrule 80 instead of ferrule 20. Like features in FIG. 8 have the same numbers as the corresponding features in FIG. 5. As shown in FIG. 8, the assembly 800 is connected together, such that the threaded portion 21 of fitting 30 is engaged with the threaded portion 4 of nut 10, such that the tapered first end 82 of the ferrule 80 is compressed and held against the tapered portion 2 of the nut 10, and the tapered second end 84 of the ferrule 80 is compressed and held against the tapered portion 22 of the fitting 30. Tubing 50 extends through the passageways 7, 81, and 27 of the nut 10, ferrule 80, and the fitting 30, respectively. The tapered first end 82 of the ferrule 80 is compressed against and securely holds the tubing 50 in place in the assembly 800 when assembly 800 is connected. Similarly, the tapered second end 84 of the ferrule 80 is compressed against and provides a leak proof fluid seal with the tapered portion 22 of the fitting 30. Thus, the assembly 800 provides a leak proof connection of the tubing 50 to a port of an LC or other AI system, or to another fitting or connection in an LC or other AI system.

Figure 9:
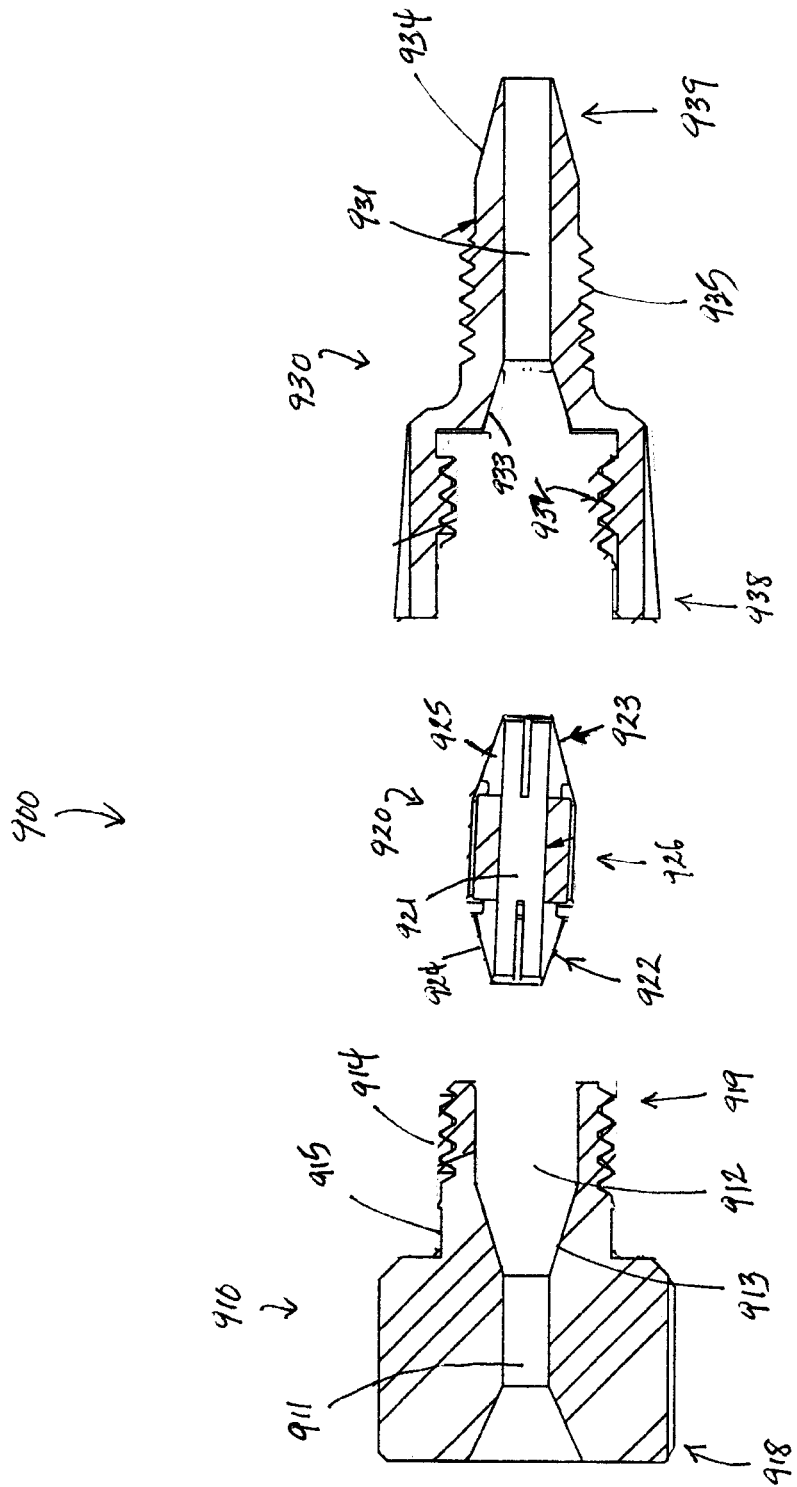
FIG. 9 is an exploded cross-sectional view of an alternative embodiment of an assembly.

Now referring to FIG. 9, an alternative embodiment of an assembly 900 is shown. Like features and elements in the drawings have the same numerals in the various figures. FIG. 9 provides an exploded cross-sectional view of nut 910, ferrule 920 and fitting 930. Each of nut 910, ferrule 920, and fitting 930 have internal passageways 911, 921, and 931, respectively, extending therethrough. The passageways 911, 921, and 931 are adapted to allow tubing (not shown) to extend through each of nut 910, ferrule 920, and fitting 930, and thus through the assembly 900.

As shown in FIG. 9, nut 910 has a first end 918 and a second end 919, and includes an interior portion 912 at its second end 919. A portion of the interior portion 912 includes an internal tapered portion 913. The tapered portion 913 of the nut 910 is adapted to receive and securely hold the first end portion 922 of the ferrule 920 when the assembly 900 is made. Nut 910 also includes external threaded portion 914. The threads of the external threaded portion 914 of the nut 910 are adapted to removably receive and securely hold the internal threaded portion 932 of the fitting 930 when the assembly 900 is connected. The nut 910 further includes an exterior portion 915.

In FIG. 9, it can be seen that the fitting 930 has a first end 938 and a second end 939, and further has an internal tapered portion 933 near the first end 938, opposite the externally tapered end portion 934 of the second end 939 of the fitting 930. The internally tapered portion 933 of the fitting 930 is adapted to receive and removably hold the second end portion 923 of the ferrule 920 when the assembly 900 is made. The fitting 930 further includes an internal threaded portion 932 near the first end 938, and an external threaded portion 935 between first end 938 and second end 939, and a tapered portion 934 near the second end 939 of fitting 930.

With respect to the ferrule 920 shown in FIG. 9, the ferrule 920 has a first end 922 with an externally tapered portion 924, a middle portion 926 that is not tapered, and a second end 923 with an external tapered portion 925. Although not shown, it will be appreciated that the angles of tapered portions 924 and 925 of the ferrule 920 from the axis of ferrule 920 may differ from the angles defined by the tapered portions 913 and 933 of the nut 910 and the fitting 930, respectively. For example, the angles defined by the tapered portions 924 and 925 may be greater than the angles defined by tapered portions 913 and 933, respectively, to make it easier to obtain sufficient tubing retention with assembly 900 when nut 910, ferrule 920, and fitting 930 are engaged and assembled.

Figure 10:
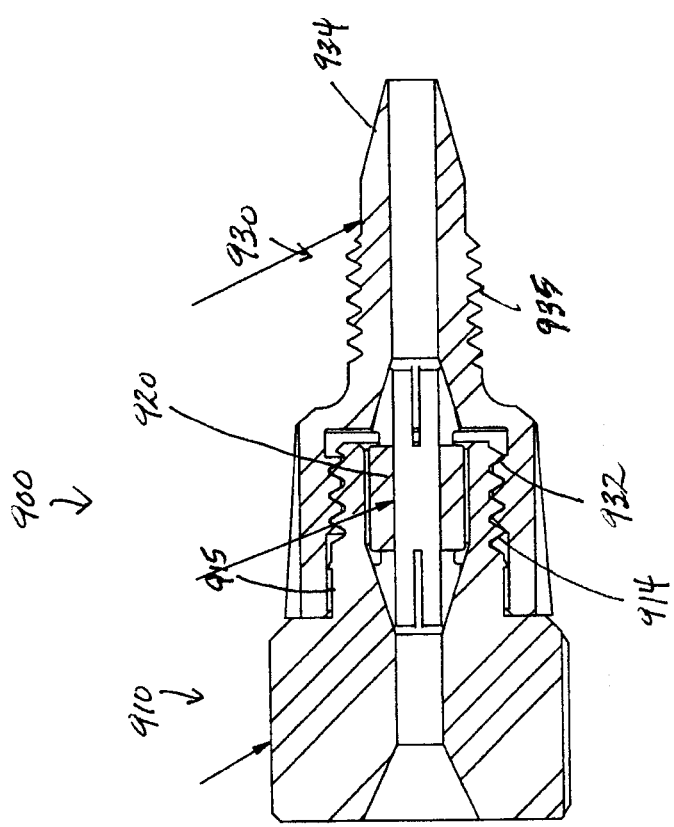
FIG. 10 is a cross-sectional view of the alternative embodiment of an assembly shown in FIG. 9 when connected.

Referring now to FIG. 10, a cross-sectional view of the assembly 900 as shown in FIG. 9 as connected by an operator is shown. Nut 910, ferrule 920, and fitting 930 are removably secured to one another. At least a portion of the internal threaded portion 932 of the fitting 930 receives and holds at least a portion of the external threaded portion 914 of the nut 910. As noted above, the threaded portions 914 and 932 are each adapted to mate with each other, such that a connection can easily be made as shown in FIG. 10. In addition, at least a portion of the fitting 930 extends to the exterior portion 915 of the nut 910. The fitting 930 includes an external threaded portion 935 of the portion of the fitting 930 that extends outward from the nut 910, as well as a tapered portion 934. The tapered portion 934 of the fitting 930 is adapted to fit within a port (not shown) of an LC or other AI component or fitting, and the threaded portion 935 is adapted to mate with an internally threaded portion (not shown) of the port of an LC system component or a fitting or other component of an LC or other AI system.

Figure 11:
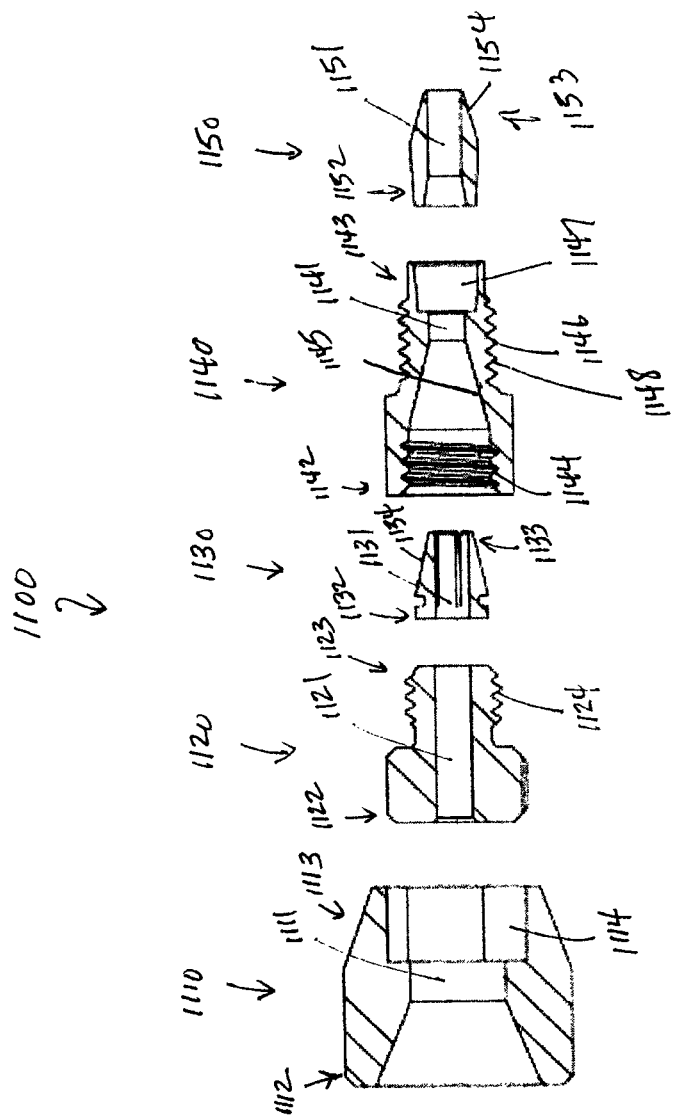
FIG. 11 is an exploded cross-sectional view of an alternative embodiment of an assembly.

Now referring to FIG. 11, an alternative embodiment of an assembly 1100 is shown. Like features and elements in the drawings have the same numerals in the various figures. FIG. 11 provides an exploded cross-sectional view of removable knurl head 1110, nut 1120, ferrule 1130, fitting 1140, and replaceable ferrule tip 1150. Each of removable knurl head 1110, nut 1120, ferrule 1130, fitting 1140, and replaceable ferrule tip 1150 have internal passageways 1111, 1121, 1131, 1141, and 1151, respectively, extending therethrough. The passageways 1111, 1121, 1131, 1141, and 1151 are adapted to allow tubing (not shown) to extend through each of removable knurl head 1110, nut 1120, ferrule 1130, fitting 1140, and replaceable ferrule tip 1150, and thus through the assembly 1100.

As shown in FIG. 11, removable knurl head 1110 has a first end 1112 and a second end 1113, and includes an internal portion 1114 at the second end 1113. The internal portion 1114 of removable knurl head 1110 is adapted to receive first end 1122 of nut 1120 when the assembly 1100 is connected. Nut 1120 has a first end 1122 and a second end 1123, and includes an external threaded portion 1124. The threads of the external threaded portion 1124 of the nut 1120 are adapted to removably receive and securely hold the internal threaded portion 1144 of the fitting 1140 when the assembly 1100 is connected.

In FIG. 11, it can be seen that the fitting 1140 has a first end 1142 and a second end 1143, and further has an internal tapered portion 1145 near the first end 1142. The internally tapered portion 1145 of the fitting 1140 is adapted to receive and removably hold the second end portion 1133 of the ferrule 1130 when the assembly 1100 is made. The fitting 1140 further includes an internal threaded portion 1144 near the first end 1142, and an external threaded portion 1146 near the second end 1143. Fitting 1140 includes an internal portion 1147 at the second end 1143. The internal portion 1147 of fitting 1140 is adapted to receive first end 1152 of ferrule tip 1150 when the assembly 1100 is connected.

With respect to the ferrule 1130 shown in FIG. 11, the ferrule 1130 has a first end 1132 and a second end 1133 with an external tapered portion 1134. Although not shown, it will be appreciated that the angle of tapered portion 1134 of the ferrule 1130 from the axis of ferrule 1130 may differ from the angles defined by the tapered portion 1145 of the fitting 1140. For example, the angle defined by the tapered portion 1134 may be greater than the angle defined by tapered portion 1145 to make it easier to obtain sufficient tubing retention with assembly 1100 when nut 1120, ferrule 1130, and fitting 1140 are engaged and assembled. The replaceable ferrule tip 1150 has a first end 1152 and a second end 1153, and an external tapered portion 1154 at second end 1153.

Figure 12:
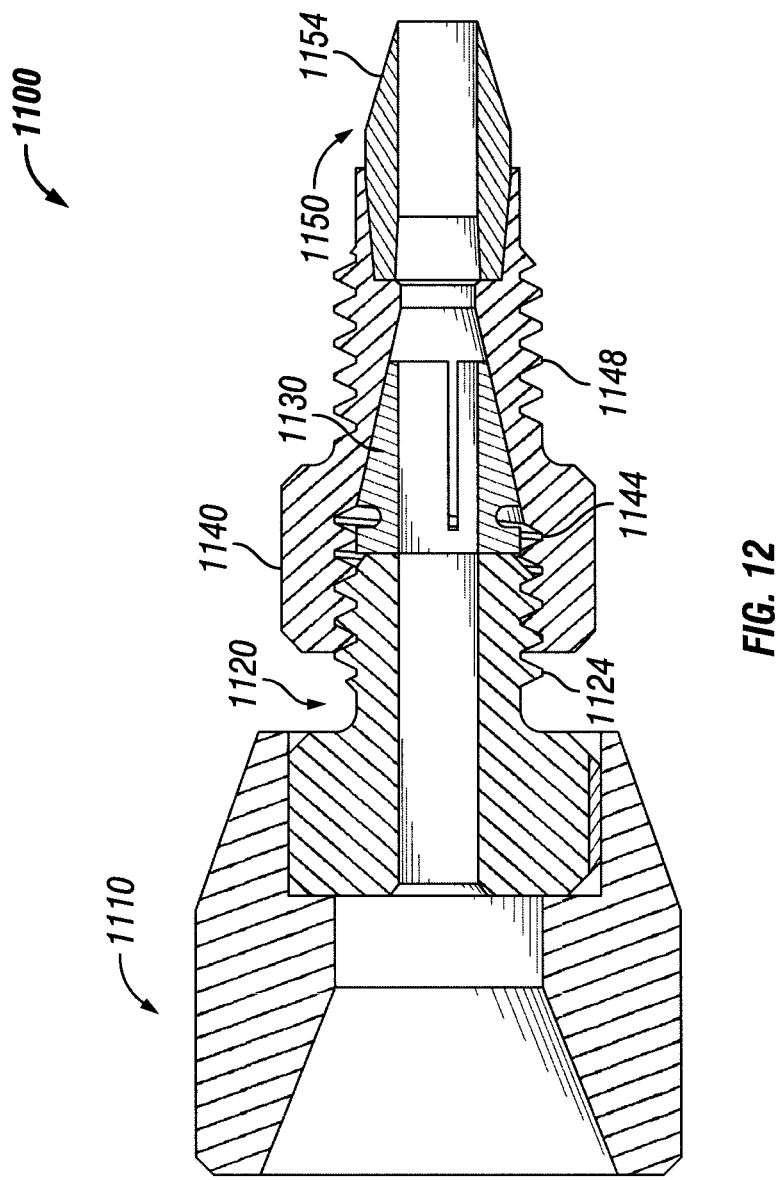
FIG. 12 is a cross-sectional view of the alternative embodiment of an assembly shown in FIG. 11 when connected.

Referring now to FIG. 12, a cross-sectional view of the assembly 1100 as shown in FIG. 11 as connected by an operator is shown. Removable knurl head 1110, nut 1120, ferrule 1130, fitting 1140, and replaceable ferrule tip 1150 are removably secured to one another. At least a portion of the internal threaded portion 1144 of the fitting 1140 receives and holds at least a portion of the external threaded portion 1124 of the nut 1120. As noted above, the threaded portions 1124 and 1144 are each adapted to mate with each other, such that a connection can easily be made as shown in FIG. 12. The fitting 1140 includes an external threaded portion 1148 of the portion of the fitting 1140 that extends outward from the nut 1120. The tapered portion 1154 of the replaceable ferrule tip 1150 is adapted to fit within a port (not shown) of an LC or other AI component or fitting, and the threaded portion 1148 is adapted to mate with an internally threaded portion (not shown) of the port of an LC system component or a fitting or other component of an LC or other AI system.

In testing of assemblies like those shown and described herein, good results have been obtained. In a first series of tests, assemblies like those shown in FIG. 5 were assembled, in which the tubing was made of stainless steel, while the nut 10, ferrule 20, and fitting 30 were made of PEEK. We used a torque wrench manufactured and available from Tohnichi, model 20STC-A, to measure the torque used to connect the test assemblies. In this first series of tests, we connected a Haskell test stand, with one side of the tee connected to a Honeywell pressure transducer. The other side of the tee was connected to the assembly being tested. We filled the assemblies with water and connected the open end of the tubing to a union that was plugged. The torque used to connect each of the assemblies was controlled and measured during the connection process by the Tohnichi torque wrench. We then pressurized the assemblies and measured the pressures withstood before failure was detected. In the first series of tests, assemblies like those shown in FIG. 5 were connected with about four inch-pounds of torque, and such assemblies withstood a pressure, on average, of over 18,000 psi. In a second series of tests, we repeated the procedure described, except that five inch-pounds of torque were applied to connect the assemblies. In this second series of tests, the assemblies so made, like those shown in FIG. 5, withstood an average pressure of almost 25,000 psi. In still a third series of tests, we used the foregoing procedure, except that we tested a series of assemblies like those shown in FIG. 8. In this third series of tests, we applied about four inch-pounds of torque to connect the assemblies, like those shown in FIG. 8 and found that such assemblies withstood an average of over 23,000 psi. Because a human operator can exert forces of four or five inch-pounds of torque, an operator can connect the assembly 1 to obtain a leak proof connection without the use of tools such as wrenches, pliers or the like, thereby allowing the operator to more easily and quickly make or break such connections in UHPLC systems. Moreover, because a polymer can be used for ferrule 20 (and ferrule 80 as well), the assembly 1 is considered advantageous because there is less chance of deforming the tubing 50 and adversely affecting the flow rate of fluid through the tubing 50 or affecting the characteristics of the fluid flow through tubing 50 (e.g., creating turbulent flow instead of laminar flow).

While the present invention has been shown and described in various embodiments, those skilled in the art will appreciate from the drawings and the foregoing discussion that various changes, modifications, and variations may be made without departing from the spirit and scope of the invention as set forth in the claims. Hence the embodiments shown and described in the drawings and the above discussion are merely illustrative and do not limit the scope of the invention as defined in the claims herein. The embodiments and specific forms, materials, and the like are merely illustrative and do not limit the scope of the invention or the claims herein.

We claim:

1. A fitting assembly for use in a liquid chromatography system, comprising:
   a) a nut having a first end and a second end, and having a passageway therethrough, wherein said second end of said nut comprises an externally threaded portion;
   b) a ferrule having a first end and a second end and having a passageway therethrough, wherein said second end of said ferrule comprises an externally tapered portion;
   c) a fitting having a first end and a second end and having a passageway therethrough, wherein the first end of said fitting comprises an internally threaded portion and said fitting further comprises an internally tapered portion, and wherein the internally threaded portion of said fitting is adapted to securely engage with the externally threaded portion of said nut, and wherein the internally tapered portion of said fitting is adapted to receive and hold the externally tapered portion of said ferrule, and wherein said second end of said fitting defines an opening; and
   d) a ferrule tip having a first end and an second end, wherein said second end of said ferrule tip comprises an externally tapered portion, and wherein at least a portion of said first end of said ferrule tip is adapted to securely engage within the opening in said second end of said fitting.

2. The fitting assembly according to claim 1, wherein said fitting further comprises an external tapered portion located at or near the second end of said fitting.

3. The fitting assembly according to claim 1, wherein said fitting further comprises an externally threaded portion which is located between the first end of said fitting and the second end of said fitting.

4. The fitting assembly according to claim 1, wherein said nut, said fitting, or said ferrule comprises a polymer.

5. The fitting assembly according to claim 1, wherein at least one of said first end and said second end of said ferrule comprises a plurality of members.

6. The fitting assembly according to claim 1, wherein said passageway through said nut, said ferrule, said fitting, or said ferrule tip comprises a coating.

7. The fitting assembly according to claim 6, wherein the coating comprises a nickel, silica carbide, copper or diamond coating, or a combination thereof.

8. The fitting assembly of claim 1, further comprising a knurl head having a first end and a second end and a passageway therethrough, wherein said second end of said knurl head defines an opening adapted to securely engage with said first end of said nut.

9. The fitting assembly according to claim 8, wherein said passageway through said knurl head comprises a coating.

10. The fitting assembly according to claim 1, wherein at least one of said nut, ferrule, and fitting comprise a metal.

11. The fitting assembly fitting assembly according to claim 1, wherein at least one of said nut, ferrule, and fitting comprise (PEEK) and at least one of said nut, ferrule, and fitting comprise steel.

12. The fitting assembly according to claim 1, where the tapered portion of said nut defines a first angle from the axis of said nut, and the tapered portion of the first end of said ferrule defines a second angle from the axis of said ferrule, and wherein the first angle is not the same as the second angle.

13. A fitting assembly for use in a liquid chromatography system, comprising:
   a) a nut having a first end and a second end, and having a passageway therethrough, wherein said second end of said nut comprises a threaded portion;
   b) a ferrule having a first end and a second end and having a passageway therethrough, wherein said second end of said ferrule comprises an externally tapered portion;
   c) a fitting having a first end and a second end and having a passageway therethrough, wherein the first end of said fitting comprises a threaded portion and said fitting further comprises an internally tapered portion, and wherein the threaded portion of said fitting is adapted to securely engage with the threaded portion of said nut, and wherein the internally tapered portion of said fitting is adapted to receive and hold the externally tapered portion of said ferrule, and wherein said second end of said fitting defines an opening; and
   d) a ferrule tip having a first end and an second end, wherein said second end of said ferrule tip comprises an externally tapered portion, and wherein at least a portion of said first end of said ferrule tip is adapted to be received within the opening in said second end of said fitting.

14. The fitting assembly according to claim 13, wherein said passageway through said nut, said ferrule, said fitting, or said ferrule tip comprises a coating.

15. The fitting assembly according to claim 14, wherein said passageway through said nut, said ferrule, said fitting, or said ferrule tip comprises a nickel, silica carbide, copper or diamond coating, or a combination thereof.

16. The fitting assembly of claim 13, further comprising a knurl head having a first end and a second end and a passageway therethrough, wherein said second end of said knurl head defines an opening adapted to securely engage with said first end of said nut.

17. The fitting assembly according to claim 16, wherein said passageway through said knurl head comprises a coating.

18. The fitting assembly according to claim 13, wherein at least one of said nut, ferrule, and fitting comprise a metal.

19. The fitting assembly according to claim 13, wherein at least one of said nut, ferrule, and fitting comprise polyetheretherketone (PEEK) and at least one of said nut, ferrule, and fitting comprise steel.

20. The fitting assembly according to claim 13, where the tapered portion of said nut defines a first angle from the axis of said nut, and the tapered portion of the first end of said ferrule defines a second angle from the axis of said ferrule, and wherein the first angle is not the same as the second angle.

* * * * *